United States Patent [19]

Buchholz

[11] Patent Number: 5,610,266
[45] Date of Patent: Mar. 11, 1997

[54] COPOLYMERS OF TRIMETHYLENECARBONATE AND OPTIONALLY INACTIVE LACTIDES

[75] Inventor: Berthold Buchholz, Ingelheim am Rhein, Germany

[73] Assignee: Boehringer Ingelheim KG, Ingelheim am Rhein, Germany

[21] Appl. No.: 479,492

[22] Filed: Jun. 7, 1995

Related U.S. Application Data

[63] Continuation of Ser. No. 342,662, Nov. 18, 1994, abandoned, which is a continuation of Ser. No. 204,722, Mar. 2, 1994, abandoned, which is a continuation of Ser. No. 73,835, Jun. 8, 1993, abandoned, which is a continuation of Ser. No. 942,542, Sep. 9, 1992, abandoned, which is a continuation of Ser. No. 824,430, Jan. 23, 1992, abandoned, which is a continuation of Ser. No. 610,616, Nov. 8, 1990, abandoned.

[30] Foreign Application Priority Data

Nov. 9, 1989 [DE] Germany ............... 39 37 272.3

[51] Int. Cl.$^6$ ............................................. C08G 63/08
[52] U.S. Cl. ................... 528/354; 528/480; 528/481; 528/499; 528/355
[58] Field of Search ................................. 528/480, 481, 528/499, 354, 355

[56] References Cited

U.S. PATENT DOCUMENTS

| 4,810,775 | 3/1989 | Bendix et al. | 528/480 |
| 4,960,866 | 10/1990 | Bendix et al. | 528/499 |
| 4,983,745 | 1/1991 | Muller et al. | 549/274 |

*Primary Examiner*—Shelley A. Dodson
*Attorney, Agent, or Firm*—Robert P. Raymond; Wendy E. Rieder; Alan R. Stempel

[57] ABSTRACT

The present invention relates to new copolymers of trimethylenecarbonate and optically inactive lactides, the preparation and use thereof.

3 Claims, No Drawings

COPOLYMERS OF TRIMETHYLENECARBONATE AND OPTIONALLY INACTIVE LACTIDES

This is a continuation, application Ser. No. 342,662, filed Nov. 18, 1994, now abandoned, which is a continuation of application Ser. No. 204,722, filed Mar. 2, 1994, now abandoned, which is a continuation of application Ser. No. 073,835, filed Jun. 8, 1993, now abandoned, which is a continuation of application Ser. No. 942,542, filed Sep. 9, 1992, now abandoned, which is a continuation of application Ser. No. 824,430, filed Jan. 23, 1992, now abandoned, which is a continuation of application Ser. 610,616, filed Nov. 8, 1990, now abandoned.

The invention relates to new copolymers of trimethylenecarbonate (1,3-dioxan-2-one) and optically inactive lactides, namely meso-lactide and D,L-lactide, the preparation and use thereof.

The use of trimethylenecarbonate polyesters for preparing a plurality of surgical objects is known. In connection with this, attempts have frequently been made, when using copolymers of trimethylenecarbonate, to modify the properties of the resulting polyesters to suit the particular application by a suitable choice of one or other of the comonomers.

Thus, copolymers of trimethylenecarbonate (TMC) with lactides such as glycolide or L-lactide are known from the prior art.

For example, U.S. Pat. No. 4,705,820 discloses a so-called "random polymer" synthesised from trimethylenecarbonate and glycolide units.

U.S. Pat. No. 4,652,264 relates to a surgical prosthesis made from a biodegradable fibre material. The fibres consist of a copolymer consisting of up to 50% trimethylenecarbonate units, the above-mentioned lactides being used as other comonomers.

U.S. Pat. No. 4,633,873 describes the use of a polyester of trimethylenecarbonate and glycolide units for the preparation of a flexible surgical aid.

U.S. Pat. No. 4,429,080 relates to biodegradable filaments for fabric prepared from a block polymer consisting of trimethylenecarbonate and glycolide blocks.

U.S. Pat. No. 4,300,656 relates to surgical objects made from a polymer which is synthesised essentially from glycolide units. Trimethylenecarbonate (TMC) is also described as another suitable comonomer.

Similarly, German Offenlegungsschrift 28 50 824 discloses a copolymer prepared from glycolide and trimethylenecarbonate (TMC) which is also used in the preparation of surgical fixing elements.

German Patent 28 21 570 discloses a process for preparing copolymers in which the individual monomers are added sequentially during polymerisation so as to obtain specific properties in the finished copolymer.

However, the prior art contains no references to the use of trimethylenecarbonate (TMC) and meso- and/or D,L-lactide.

Surprisingly, it has now been found that by using D,L-lactide or meso-lactide as comonomers in copolymerisation with trimethylenecarbonate (TMC), the properties of the resulting copolymer can easily be influenced in a number of ways without the need for special polymerisation techniques or procedural measures.

The new copolymers based on trimethylenecarbonate (1,3-dioxan-2-one) units and meso-lactide and/or D,L-lactide units have between 1 and 99% by weight of trimethylenecarbonate units and preferably between 4 and 90% by weight of trimethylenecarbonate units and between 10 and 96% by weight of units based on mesolactide and/or D,L-lactide. The copolymer may also contain a smaller additional amount of units of another monomer selected from the group comprising the lactides or lactones.

As can be seen from a comparison of the figures in Table 1, the mechanical properties of the copolymers according to the invention can be influenced within wide limits by varying the proportions of lactide and trimethylenecarbonate (TMC) used. Thus, copolymers containing a large proportion (>90%) of D,L-lactide are materials with comparatively high strength. However, compared with pure poly(D,L-lactide) the copolymers according to the invention are characterised by increased viscosity (no brittle fracture).

Polymers containing a moderate amount of D,L-lactide (between about 30 and 70% D,L-lactide) are exceptionally expansible materials. The values for elongation at break and for elongation under maximum tension reach their peak as the proportion of lactide is reduced (see Table 1).

As the proportion of lactide is reduced (<30%) the mechanical properties of the copolymers are substantially similar to those of pure polytrimethylene-carbonate (poly-TMC) and therefore copolymers containing a proportion of lactide of >30% are particularly preferred. Depending on the mechanical properties sought (strong and tough or resilient) polymers with a high or moderate proportion of lactide, which are amorphous by nature, are particularly preferred.

The copolymers according to the invention may be produced by statistical (random) polymerisation as well as by sequential polymerisation. For example, randomly polymerised poly(D,L-lactide-co-trimethylenecarbonate), poly-(meso-lactide-co-trimethylenecarbonate)-polymers and AB-, ABA-block polymers may be prepared from poly-(meso-lactide-co-trimethylenecarbonate).

The biodegradable polymerisation products resulting from the copolymerisation in each case exhibit an amorphous nature, whilst, depending on the choice of the lactide and the ratio of trimethylenecarbonate (TMC) to meso- or D,L-lactide, the glass transition temperature of the copolymers according to the invention is in the range from about −20° C. to about +55° C., preferably in the range from −15° to +50° C. and particularly preferably in the range from −13° to +45° C., determined by differential thermoanalysis with a heating rate of 5 K/min. The values for inherent viscosity of the copolymers according to the invention, measured in a 0.1% solution in chloroform at 25° C., are in the range from 0.5 to 3 dl/g, preferably in the range from 0.6 to 2.5 dl/g and, particularly preferably, in the range from 0.7 to 2.1 dl/g. Depending on the particular glass transition temperature, the copolymers according to the invention have specific elasticity features which render them suitable for use in a plurality of applications.

Moreover, by suitable choice of the reaction conditions the molar mass and the composition of the copolymer as well as the sequence of the trimethylene-carbonate or lactide units can be influenced. By influencing the sequence of the trimethylenecarbonate and lactide units it is also possible to modify the in vivo properties of the surgical objects prepared from the copolymers.

Other possible ways of modifying specific characteristics of the resulting copolymers consist for example in the addition of plasticisers or other suitable polymeric additives known from the prior art.

In view of their elastic properties the copolymers according to the invention are particularly suitable for use in the form of:

1) A coating material for surgical suturing material or fixing elements. Such coatings increase the sliding qualities of the suturing material and give it better knotting properties.

The copolymers according to the invention can easily be applied to the surgical aids in question, e.g. by application in the form of a solution or by application using thermal methods. Both methods are known from the prior art.

One particularly advantageous feature is the fact that the copolymers are soluble in numerous solvents. Suitable solvents include, for example, not only chlorinated hydrocarbons but also physiologically acceptable solvents such as acetone, ethyl acetate and propylene carbonate (4-methyl-1,3-dioxolan-2-one).

2) Resorbable films for wound covering, e.g. for treating burns or areas of scraped skin. For this purpose, the copolymers according to the invention may if desired also act as carrier materials for drugs such as anti-inflammatory or bactericidal agents; however, it is also possible to use other pharmaceutical preparations.

In injuries to the skin of this kind it has hitherto been necessary to put on a dressing, always taking care to prevent the non-absorbable dressing from being incorporated into the newly formed tissue.

Since the copolymers according to the invention are resorbable if parts of the bandage should enter the plane of regeneration, the tissue will regenerate and absorb the copolymer, whilst the non-resorbed copolymer will be rejected with the scab.

In view of their elasticity and solubility characteristics, the compounds according to the invention are particularly suitable as spray dressings, for covering small wounds.

3) Elastically resorbable implants:

Thus, the copolymers according to the invention may be used, for example, as pads, bandages or sponges used in surgical operations. Surgical aids of this kind are needed in a variety of surgical operations. The use of these aids has proved particularly advantageous when the intention is to remove these aids during or after the operation, but when a part of the aid may be left behind by accident or chance. Thus, one of the complications which may occur in operations is the chance that cotton fibres from cotton swabs may be left behind in the wound. If aids made from the copolymers according to the invention are used, on the other hand, any fragments which become detached will be resorbed without any harmful consequences.

Since the composition or sequence of the individual comonomers can be used to influence the in vivo properties, i.e. including the breakdown characteristics, of the copolymers without any great effort, these comonomers are particularly suitable for applications in which a prosthesis or bandage is required as a temporary measure, e.g. devices for haemostasis, facial prostheses, patches for intestinal ruptures (hernias), dental packings, etc.

4) Carriers or containers for drugs or as retarding aids for active substance release systems in which controlled release of the drug is desired.

In active substance release systems of this kind it is desirable that the container or carrier material should dissolve during or after the release of the active substance leaving no undesirable or even pharmacologically harmful residues in the tissue. Release systems of this kind may be designed not only as an implant but also for oral administration or for administration in the form of an aerosol.

Possible methods of charging the copolymers according to the invention with active substance or of designing the active substance release systems from the outset in order to achieve the desired release characteristics are known from the prior art.

It is also possible to use the copolymers according to the invention as carriers or containers, inter alia, for agrochemicals, herbicides or insecticides.

In view of their properties of elasticity, the copolymers according to the invention are suitable, for example, for use in the form of films or plasters for use in transdermal active substance release systems. Possible ways of presenting the copolymers according to the invention as systems for the release of active substance, e.g. in the form of implants or boli, are also known from the prior art.

The copolymers according to the invention are prepared as random or block polymers and the surgical objects are prepared in conventional manner—see the prior art mentioned above. The surgical objects thus obtained are also used similarly. The examples which follow are intended to illustrate the invention without restricting it:

EXAMPLE 1

2.5 g of trimethylenecarbonate, 2.5 g of D,L-lactide and 0.25 ml of a solution of tin octoate (tin(II)-2-ethylhexanoate) in toluene (136.5 mg in 20 ml) are added successively to a glass test tube. The test tube is evacuated several times to eliminate the solvent. The test tube is sealed by fusion under a nitrogen atmosphere, suspended in an oil bath maintained at a temperature of 190° C. and kept there for 2.5 hours. After being cooled to ambient temperature, the glass test tube is broken open and any glass adhering to the polymer is removed. To remove unreacted monomer the polymer is re-precipitated from chloroform/petroleum ether and dried in vacuo.

Investigation by NMR spectroscopy (250 MHz-$^1$H-NMR, CDCl$_3$) gives a level of reaction of 96% for D,L-lactide and 97% for trimethylenecarbonate. The polymer consists of 51% by weight of trimethylenecarbonate units. The crude product has an inherent viscosity of 1.05 dl/g (measured in a 0.1% solution in chloroform at 25° C.). The purified polymer has a glass transition temperature of +9° C. (DSC, heating rate 5 K/min.).

EXAMPLES 2 TO 13

Statistical copolymers of trimethylenecarbonate and D,L-lactide in various compositions are prepared using the method of Example 1:

| Example | Batch size | Quantity of trimethylene-carbonate used | Inherent viscosity[1] |
|---|---|---|---|
| 2 | 5 g | 5% | 1.23 |
| 3 | 5 g | 10% | 1.36 |
| 4 | 100 g | 13% | 1.68 |
| 5 | 5 g | 20% | 1.11 |
| 6 | 100 g | 31% | 1.17 |
| 7 | 5 g | 40% | 0.86 |
| 8 | 100 g | 50% | 1.15 |
| 9 | 5 g | 60% | 1.15 |
| 10 | 100 g | 69% | 1.13 |
| 11 | 5 g | 80% | 1.23 |
| 12 | 100 g | 88% | 1.27 |
| 13 | 5 g | 95% | 1.82 |

[1]Amounts in dl/g measured in a 0.1% solution in chloroform at 25° C. The values for the 5 g batches refer to the crude products and, in the 100 g batches, to the purified polymers.

EXAMPLES 14 TO 16

Statistical copolymers of trimethylenecarbonate and meso-lactide (batch size 5 g, catalyst: tin octoate):

| Example | Reaction time | Quantity of trimethylene-carbonate used | Quantity of catalyst[1] | Inherent viscosity[2] |
|---------|---------------|----------------------------------------|------------------------|----------------------|
| 14 | 50 h | 30% | 50 ppm | 1.82 |
| 15 | 20 h | 50% | 200 ppm | 2.02 |
| 16 | 20 h | 70% | 200 ppm | 1.75 |

[1] Amounts in ppm Sn
[2] Amounts in dl/g, measured in a 0.1% solution in chloroform at 25° C. The values refer to the crude products.

Analytical data relating to the copolymers prepared in Examples 2 to 16:

| Example | Degree of reaction TMC[1] | Degree of reaction Lactide | Polymer composition % by wt. TMC units | Glass transition temperature [°C.] |
|---------|---------------------------|------|------|------|
| 2 | 25% | 94% | 4% | |
| 3 | 55% | 94% | 6% | +41 |
| 4 | 65% | 95% | 9% | |
| 5 | 84% | 95% | 17% | +26 |
| 6 | 92% | 96% | 30% | +23 |
| 7 | 95% | 96% | 42% | |
| 8 | 97% | 97% | 50% | +9 |
| 9 | 98% | 96% | 62% | |
| 10 | 98% | 98% | 70% | −2 |
| 11 | 98% | [2] | | |
| 12 | 98% | [2] | 90% | −13 |
| 13 | 98% | [2] | | |
| 14 | 97% | 99% | 30% | +13 |
| 15 | 97% | 99% | 50% | +4 |
| 16 | 98% | 99% | 71% | −4 |

[1] TMC: trimethylenecarbonate
[2] In Examples 11 to 13 the lactide conversion cannot be determined with sufficient accuracy by $^1$H-NMR spectroscopy.

EXAMPLE 17

Block polymer of trimethylenecarbonate and D,L-lactide:

95 g of trimethylenecarbonate and 1.90 ml of a solution of 853 mg of tin octoate in 50 ml of toluene are added successively to a glass flask. It is evacuated several times to remove the solvent and then ventilated with nitrogen. The flask is suspended in an oil bath maintained at a temperature of 190° C. During polymerisation the mixture is stirred with a stainless steel stirrer and a gentle nitrogen current is introduced. After two hours, 190 g of D,L-lactide are added. After a further two hours the highly viscous contents of the flask are poured out and left to cool.

The NMR spectroscopic investigation (250 MHz-$^1$H-NMR, CDCl$_3$) gives a reaction extent of 44% for D,L-lactide and 97% for trimethylenecarbonate.

In order to remove unreacted amounts of monomer the crude product is precipitated twice from chloroform/petroleum ether. The purified polymer has an inherent viscosity of 0.77 dl/g (measured in a 0.1% solution in chloroformat 25° C.) and consists of 54% by weight mol-% of trimethylenecarbonate units (250 MHz-$^1$H-NMR).

TABLE 1

Tensile tests on poly(D,L-lactide-co-TMC)
(carried out at ambient temperature on fusion-moulded test pieces measuring 180 × 15 × 2 mm)

| Material | Composition | $\sigma_{zM}$[1] | $\sigma_{zR}$[2] | $\epsilon_{zM}$[3] | $\epsilon_{zR}$[4] |
|----------|-------------|------|------|------|------|
| P—TMC[5] | | 1.3 | 0.9 | 85 | 193 |
| P—(TMC/DL—LA)[6] | 90/10 | 1.2 | 1.0 | 84 | 166 |
| P—(TMC/DL—LA) | 70/30 | 1.6 | 1.2 | 104 | 226 |
| P—(TMC/DL—LA) | 50/50 | 5.2 | 5.2 | 963 | 963 |
| P—(TMC/DL—LA) | 30/70 | 14 | 14 | 519 | 519 |
| P—(TMC/DL—LA) | 10/90 | 27 | 11 | 4.3 | 28 |
| P—DL—LA[7] | | 52 | 52 | 3.6 | 3.6 |

[1] $\sigma_{zM}$ = Tensile strength [N/mm$^2$]
[2] $\sigma_{zR}$ = Tear strength [N/mm$^2$]
[3] $\epsilon_{zM}$ = Elongation under maximum tension [%]
[4] $\epsilon_{zR}$ = Elongation at break [%]
[5] P—TMC = Polytrimethylenecarbonate
[6] P—(TMC/DL—LA) = Poly(trimethylenecarbonate-co-D,L-lactide)
[7] P—DL—LA = Poly-D,L-lactide

We claim:

1. A copolymer comprising trimethylenecarbonate and D,L-lactide units, wherein said copolymer contains more than 30% D,L-lactide units.

2. The copolymer according to claim 1, wherein said copolymer contains between about 30% and 96% D,L-lactide.

3. The copolymer according to claim 1, wherein said copolymer contains between about 30% and 70% D,L-lactide.

* * * * *